United States Patent
Turk, Jr. et al.

(10) Patent No.: US 10,391,229 B2
(45) Date of Patent: Aug. 27, 2019

(54) FLUID CONVEYANCE SAFETY DEVICES, METHODS, AND SYSTEMS

(71) Applicant: NxStage Medical, Inc., Lawrence, MA (US)

(72) Inventors: Joseph E. Turk, Jr., No. Andover, MA (US); Jeffrey H. Burbank, Boxford, MA (US); James M. Brugger, Newburyport, MA (US)

(73) Assignee: Nxstage Medical, Inc., Lawrence, MA (US)

( * ) Notice: Subject to any disclaimer, the term of this patent is extended or adjusted under 35 U.S.C. 154(b) by 898 days.

(21) Appl. No.: 14/945,758

(22) Filed: Nov. 19, 2015

(65) Prior Publication Data

US 2016/0144097 A1    May 26, 2016

Related U.S. Application Data

(63) Continuation of application No. 13/879,988, filed as application No. PCT/US2011/057727 on Oct. 25, 2011, now Pat. No. 9,283,320.
(Continued)

(51) Int. Cl.
*A61M 1/36* (2006.01)
*A61M 5/158* (2006.01)
(Continued)

(52) U.S. Cl.
CPC ........ *A61M 1/3659* (2014.02); *A61M 1/3653* (2013.01); *A61M 1/3656* (2014.02);
(Continued)

(58) Field of Classification Search
CPC .............. A61M 1/3659; A61M 1/3656; A61M 1/3661; A61M 1/3653; A61M 5/158; A61M 5/1583; A61M 5/3243; A61M 5/365; A61M 2005/1586; A61M 2005/1587; A61M 2005/1588; A61M 2005/3256;
(Continued)

(56) References Cited

U.S. PATENT DOCUMENTS 3,985,134 A    10/1976  Lissot et al.
4,014,333 A     3/1977  McIntyre
(Continued)

OTHER PUBLICATIONS

Hurst, "A Costly Complication: Venous Needle Dislodgement," Virgo Publishing, http://www.renalbusiness.com, posted on Sep. 22, 2010, pp. 1-6.
(Continued)

*Primary Examiner* — Philip R Wiest
(74) *Attorney, Agent, or Firm* — Potomac Law Group, PLLC; Mark A. Catan

(57) ABSTRACT

The disclosed subject matter includes a structure and method for making a dual-lumen needle from single lumen needles to take advantage of the much higher economies of scale. Variations include two needles joined by a flow junction and one needle and a single cannula joined by a flow junction. In addition disclosed are methods of using a dual-lumen needle in a two needle access for blood treatment is disclosed in which at least venous flow is provided through a dual-lumen needle with arterial flow just sufficient to provide air infiltration detection in the event of withdrawal of the dual-lumen needle.

16 Claims, 6 Drawing Sheets

Related U.S. Application Data

(60) Provisional application No. 61/406,947, filed on Oct. 26, 2010.

(51) Int. Cl.
*A61M 5/32* (2006.01)
*A61M 5/36* (2006.01)
*B29C 65/48* (2006.01)
*B29C 65/00* (2006.01)

(52) U.S. Cl.
CPC .......... *A61M 1/3661* (2014.02); *A61M 5/158* (2013.01); *A61M 5/1582* (2013.01); *A61M 5/3243* (2013.01); *A61M 5/365* (2013.01); A61M 2005/1586 (2013.01); A61M 2005/1587 (2013.01); A61M 2005/1588 (2013.01); A61M 2005/3256 (2013.01); A61M 2207/00 (2013.01); *B29C 65/48* (2013.01); *B29C 66/1122* (2013.01); *B29C 66/5221* (2013.01); *Y10T 29/49879* (2015.01)

(58) Field of Classification Search
CPC .......... A61M 2207/00; Y10T 29/49879; B29C 65/48; B29C 65/1112; B29C 65/5221
See application file for complete search history.

(56) References Cited

U.S. PATENT DOCUMENTS

| | | | |
|---|---|---|---|
| 4,134,402 A | 1/1979 | Mahurkar | |
| 4,144,884 A | 3/1979 | Tersteegen et al. | |
| 4,202,332 A | 5/1980 | Tersteegen et al. | |
| 4,403,990 A | 9/1983 | Garver et al. | |
| 4,447,227 A | 5/1984 | Kotsanis | |
| 4,614,590 A | 9/1986 | Rath et al. | |
| 4,891,044 A | 1/1990 | Mitchell | |
| 5,053,004 A | 10/1991 | Markel et al. | |
| 5,120,303 A | 6/1992 | Hombrouckx | |
| 5,207,648 A | 5/1993 | Gross | |
| 5,735,813 A | 4/1998 | Lewis | |
| 5,911,706 A | 6/1999 | Estabrook et al. | |
| 6,090,048 A | 7/2000 | Hertz et al. | |
| 6,221,040 B1 | 4/2001 | Kleinekofort | |
| 6,638,254 B2 | 10/2003 | Nakagami | |
| 6,979,317 B2 | 12/2005 | Galt et al. | |
| 7,022,110 B2 | 4/2006 | Shibata | |
| 7,025,746 B2 | 4/2006 | Tal | |
| 7,682,340 B2 | 3/2010 | Funamura et al. | |
| 2004/0153021 A1 | 8/2004 | Osborne et al. | |
| 2004/0186415 A1* | 9/2004 | Burbank | A61M 1/3653 604/6.16 |
| 2007/0135757 A1 | 6/2007 | Acker et al. | |
| 2009/0156975 A1 | 6/2009 | Robinson et al. | |
| 2009/0198171 A1* | 8/2009 | Kleinekofort | A61M 1/3653 604/6.16 |
| 2010/0076406 A1 | 3/2010 | Raulerson | |
| 2010/0191166 A1 | 7/2010 | Phillips et al. | |

OTHER PUBLICATIONS

International Search Report and Written Opinion, dated Jul. 2, 2012, for International Application No. PCT/US11/57727.

* cited by examiner

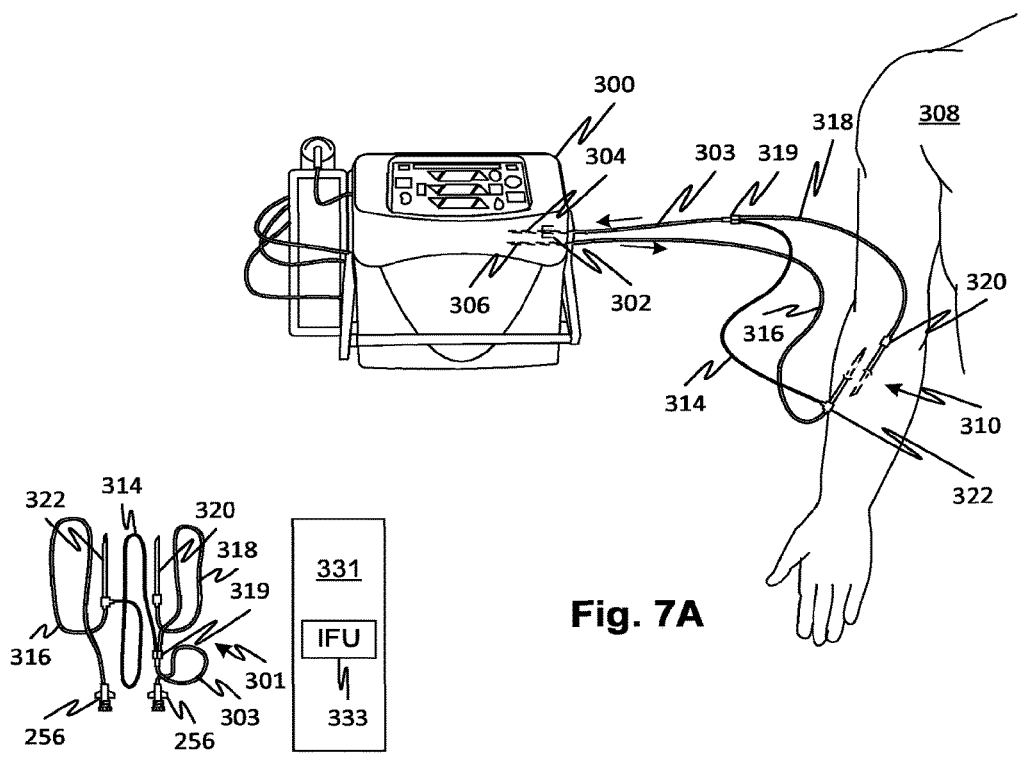
Fig. 7A
Fig. 7D
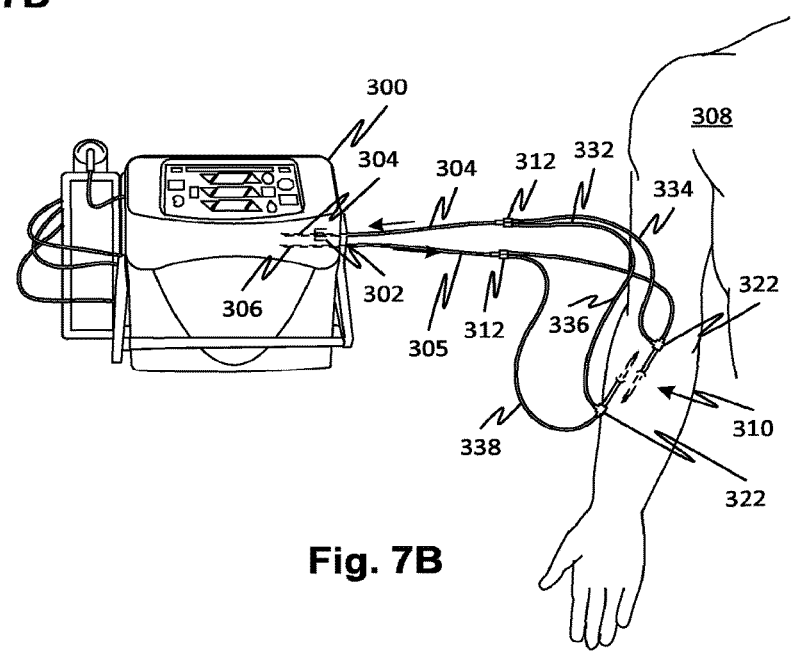
Fig. 7B

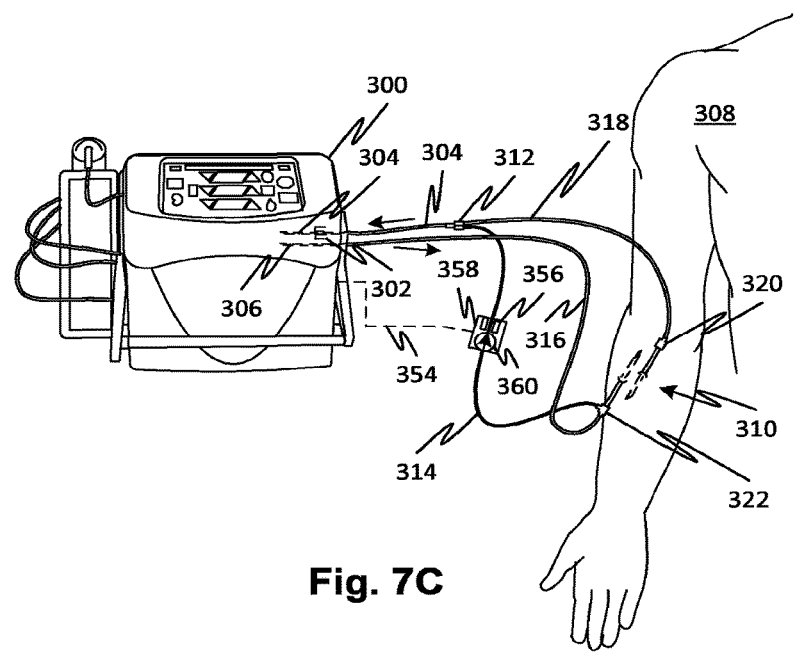
Fig. 7C
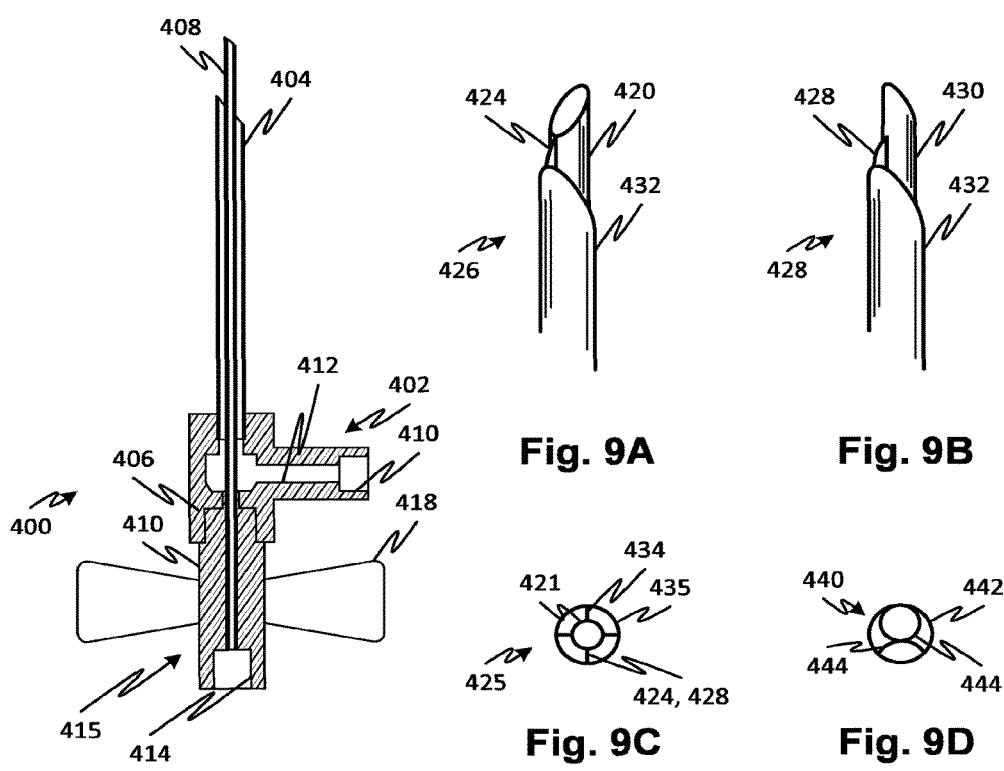
Fig. 9A  Fig. 9B
Fig. 9C  Fig. 9D
Fig. 8

FLUID CONVEYANCE SAFETY DEVICES, METHODS, AND SYSTEMS

CROSS REFERENCE TO RELATED APPLICATIONS

The present application claims the benefit of U.S. Provisional Application Ser. No. 61/406,947 filed Oct. 26, 2010, which is hereby incorporated by reference as if set forth herein in its entirety.

FIELD

The disclosed subject matter relates to the detection of leaks, for example, leaks resulting from a loss of integrity of a blood circuit.

BACKGROUND

Many medical procedures involve the extraction and replacement of flowing blood from, and back into, a donor or patient. The reasons for doing this vary, but generally, they involve subjecting the blood to some process that cannot be carried out inside the body. When the blood is outside the patient it is conducted through machinery that processes the blood. The various processes include, but are not limited to, hemodialysis, hemofiltration, hemodiafiltration, blood and blood component collection, plasmapheresis, aphresis, and blood oxygenation.

One technique for extracorporeal blood processing employs a single "access," for example a single needle in the vein of the patient or a fistula. A volume of blood is cyclically drawn through the access at one time, processed, and then returned through the same access at another time. Single access systems are uncommon because they limit the rate of processing to half the capacity permitted by the access. As a result, two-access systems, in which blood is drawn from a first access, called an arterial access, and returned through a second access, called a venous access, are much faster and more common. These accesses include catheters, catheters with subcutaneous ports, fistulas, and grafts.

The processes listed above, and others, often involve the movement of large amounts of blood at a very high rate. For example, 500 ml. of blood may be drawn out and replaced every minute, which is about 5% of the patient's entire supply. If a leak occurs in such a system, the patient could be drained of enough blood in a few minutes to cause loss of consciousness with death following soon thereafter. As a result, such extracorporeal blood circuits are normally used in very safe environments, such as hospitals and treatment centers, and attended by highly trained technicians and doctors nearby. Even with close supervision, a number of deaths occur in the United States every year due to undue blood loss from leaks.

Leaks present a very real risk. Leaks can occur for various reasons, among them: extraction of a needle, disconnection of a luer, poor manufacture of components, cuts in tubing, and leaks in a catheter. However, in terms of current technology, the most reliable solution to this risk, that of direct and constant trained supervision in a safe environment, has an enormous negative impact on the lifestyles of patients who require frequent treatment and on labor requirements of the institutions performing such therapies. Thus, there is a perennial need in the art for ultra-safe systems that can be used in a non-clinical setting and/or without the need for highly trained and expensive staff.

Currently, there is great interest in ways of providing systems for patients to use at home. One of the risks for such systems is the danger of leaks. As a result, a number of companies have dedicated resources to the solution of the problem of leak detection.

The first level of protection against return line blood loss is the use of locking luers on all connections, as described in International Standard ISO 594-2 which help to minimize the possibility of spontaneous disconnection during treatment. Care in the connection and taping of lines to the patient's bodies is also a known strategy for minimizing this risk.

A higher level of protection is the provision of venous pressure monitoring, which detects a precipitous decrease in the venous line pressure. This technique is outlined in International Standard IEC 60601-2-16. This approach, although providing some additional protection, is not very robust, because most of the pressure loss in the venous line is in the needle used to access the patient. There is very little pressure change in the venous return line that can be detected in the event of a disconnection, so long as the needle remains attached to the return line. Thus, the pressure signal is very weak. The signal is no stronger for small leaks in the return line, where the pressure changes are too small to be detected with any reliability. One way to compensate for the low pressure signal is to make the system more sensitive, as described in U.S. Pat. No. 6,221,040, but this strategy can cause many false positives. It is inevitable that the sensitivity of the system will have to be traded against the burden of monitoring false alarms. Inevitably this leads to compromises in safety. In addition, pressure sensing methods cannot be used at all for detecting small leaks.

Yet another device for checking for leaks in return lines is described in U.S. Pat. No. 6,090,048. In the disclosed system, a pressure signal is sensed at the access and used to infer its integrity. The pressure wave may be the patient's pulse or it may be artificially generated by the pump. This approach cannot detect small leaks and is not very sensitive unless powerful pressure waves are used, in which case the effect can produce considerable discomfort in the patient.

Currently, with lower staffing levels comes the increased risk of unattended leaks. Thus, there has been, and continues to be, a need in the prior art for a foolproof approach to detection of a return line leak or disconnection.

In single-access systems, loss of blood through the patient access and blood circuit can be indirectly detected by detecting the infiltration of air during the draw cycle. Air is typically detected using an ultrasonic air detector on the tubing line, which detects air bubbles in the blood. The detection of air bubbles triggers the system to halt the pump and clamp the line to prevent air bubbles from being injected into the patient. Examples of such systems are described in U.S. Pat. Nos. 3,985,134, 4,614,590, and 5,120,303.

One type of double access is provided by a two-lumen needle or catheter, such as described in U.S. Pat. Nos. 4,202,332 and 4,144,884. These use a single access point, for example a fistula. Blood is returned and drawn through a coaxial pair of channels at the end of the catheter or needle.

An example of a system that uses a dual-lumen needle for leak detection is described in US 20040186415. This publication describes a leak safe access needle and blood circuit combined in a fluid circuit with the access needle configured as a double lumen access needle whose venous line is permanently attached to the fluid circuit. The arterial line has an air detection device. In this configuration, the only way the venous line can be disconnected is for the access needle to be withdrawn from the patient, which will necessarily result in disconnection of the arterial line, which in turn will be detected by air infiltration into the arterial line. While dual-lumen needles are effective for detecting leaks, they are expensive, suffer from a recirculation problem, and tend to be limited in terms of the volume rate of blood they can handle.

SUMMARY

According to embodiments of the disclosed subject matter, a method of manufacturing a dual-lumen needle, includes providing a first single lumen needle with a first metal cannula and a first plastic hub that supports the first metal cannula; providing a junction part of plastic having three cylindrical openings, first and second of the openings being coaxial and a third opening having an axis that crosses the common axis of the first two openings. The method further includes providing a second metal cannula whose internal diameter is larger than an inner diameter of the first metal cannula. The first opening has an internal diameter approximately the same as an outer diameter of the second cannula. The second opening is sized and shaped to receive the first plastic hub. The method further includes inserting the second cannula in the first opening and inserting the first plastic hub in the second opening including the first metal cannula with the common axis of the first and second openings. The inserting operations are performed including aligning the first and second metal cannulas coaxially. The junction part is configured such that the two inserting operations forms a fluid flow channel joining the third opening for fluid communication with an annular space coaxial with and lying between the first and second metal cannulas that is isolated from the second port.

The inserting the second cannula may be performed before the inserting the first plastic hub. The inserting the second cannula may be performed after the inserting the first plastic hub. The providing a second metal cannula may include providing the second metal cannula supported by a second plastic hub, the combination of the second metal cannula and the second plastic hub defining a needle with a port configured for attachment to a fluid line, wherein the inserting of the second cannula includes inserting the second plastic hub supporting the second cannula in the first opening. The method may include solvent bonding the hub to the second opening. The hubs may have opposing wings configured for handling and taping.

According to embodiments of the disclosed subject matter, a double lumen needle has a first needle set having a resin winged hub and a first metal cannula. The first needle set winged hub has a first hub port. A second needle set has a resin winged hub and a second metal cannula. The second needle set winged hub has a second hub port. The first needle set cannula is larger than the second. The first and second needle set winged hubs having first and second cylindrical portions, the first extending along a base of the respective cannula and the second extending away from the respective cannula and forming an opening adapted for receiving a tube. A junction part has first and second recessed ports sized and shaped to receive the first and second cylindrical portions. The first needle set second cylindrical portion is inserted in the junction part first recessed port and the second needle set first cylindrical portion being inserted in the junction part second recessed port such that the second metal cannula extends into the first metal cannula. The junction part has a third recessed port in fluid communication a channel that includes an annular spaced between the first and second metal cannulas. The channel is fluidly isolated from the lumen of the second metal cannula. The junction part is configured that the second hub port is available for direct connection to a tube to form a channel with the lumen of the second metal cannula and the third recessed port is available for connection to another tube.

According to embodiments of the disclosed subject matter, a method of using first and second single lumen needles, each having a resin hub and a metal cannula, the each hub having port opposite the metal cannula. The method includes inserting the first needle cannula in a first port of a T-junction conduit and the second needle hub port in a second port of the T-junction conduit opposite the first port such that the first needle cannula extends through the T-junction conduit into the second needle cannula; bonding the first and second needle hubs to the T-junction conduit; attaching respective tubing portions to the first needle hub and a third port of the T-junction.

According to embodiments of the disclosed subject matter, a method of manufacturing a dual-lumen needle, includes providing a first single lumen needle with a first cannula and a first plastic hub that supports the first cannula; providing a junction part of plastic having three cylindrical openings, first and second of the openings being coaxial and a third opening having an axis that crosses the common axis of the first two openings. The method further includes providing a second cannula whose internal diameter is larger than an inner diameter of the first cannula. The first opening has an internal diameter approximately the same as an outer diameter of the second cannula. The second opening is sized and shaped to receive the first plastic hub. The method further includes inserting the second cannula in the first opening and inserting the first plastic hub in the second opening including the first cannula with the common axis of the first and second openings. The inserting operations are performed including aligning the first and second cannulas coaxially. The junction part is configured such that the two inserting operations forms a fluid flow channel joining the third opening for fluid communication with an annular space coaxial with and lying between the first and second cannulas that is isolated from the second port.

The inserting the second cannula may be performed before the inserting the first plastic hub. The inserting the second cannula may be performed after the inserting the first plastic hub. The providing a second cannula may include providing the second cannula supported by a second plastic hub, the combination of the second cannula and the second plastic hub defining a needle with a port configured for attachment to a fluid line, wherein the inserting of the second cannula includes inserting the second plastic hub supporting the second cannula in the first opening. The method may include solvent bonding the hub to the second opening. The hubs may have opposing wings configured for handling and taping.

According to embodiments of the disclosed subject matter, a double lumen needle has a first needle set having a resin winged hub and a first cannula. The first needle set winged hub has a first hub port. A second needle set has a resin winged hub and a second cannula. The second needle set winged hub has a second hub port. The first needle set cannula is larger than the second. The first and second needle set winged hubs having first and second cylindrical portions, the first extending along a base of the respective cannula and the second extending away from the respective cannula and forming an opening adapted for receiving a tube. A junction part has first and second recessed ports sized and shaped to receive the first and second cylindrical portions. The first needle set second cylindrical portion is inserted in the junction part first recessed port and the second needle set first cylindrical portion being inserted in the junction part second recessed port such that the second cannula extends into the first cannula. The junction part has a third recessed port in fluid communication a channel that includes an annular spaced between the first and second cannulas. The channel is fluidly isolated from the lumen of the second cannula. The junction part is configured that the second hub port is available for direct connection to a tube to form a channel with the lumen of the second cannula and the third recessed port is available for connection to another tube.

According to embodiments, the disclosed subject matter includes a method of using first and second single lumen needles, each having a resin hub and a cannula, the each hub having port opposite the cannula. The method includes inserting the first needle cannula in a first port of a T-junction conduit and the second needle hub port in a second port of the T-junction conduit opposite the first port such that the first needle cannula extends through the T-junction conduit into the second needle cannula; bonding the first and second needle hubs to the T-junction conduit; attaching respective tubing portions to the first needle hub and a third port of the T-junction.

According to embodiments of the disclosed subject matter includes a dual-lumen needle with an inner cannula having an inner lumen and an outer cannula having an inner lumen. A hub has first and second ports, the hub being configured to support the inner and outer cannulas with the outer cannula in coaxial relation to the inner cannula thereby defining an annular channel between the inner and outer cannulas. The hub is further configured to define a first fluid channel connecting the first port with the inner cannula inner lumen and second fluid channel connecting the annular space to the second port. The inner and outer cannulas are blunt tip needles adapted for use with buttonhole-type vascular accesses and the inner cannula extends through and beyond the outer cannula at a distal end thereof extending away from the hub.

The hub may be a rigid structure such that the inner and outer cannulas are held in fixed relation to each other. The inner and outer cannulas may be metal and the hub of resin. The hub may have a T shape with one of the first and second ports on the crossbar opposite the inner and outer cannulas and the other of the first and second ports on the stem. The hub may have a Y shape.

According to embodiments, the disclosed subject matter includes a method of using the above needle comprising inserting the inner and outer cannulas through a buttonhole vascular access.

According to embodiments, the disclosed subject matter includes, a dual-lumen needle with an inner cannula having an inner lumen, an outer cannula having an inner lumen, and a hub having first and second ports. The hub is configured to support the inner and outer cannulas with the outer cannula in coaxial relation to the inner cannula thereby defining an annular channel between the inner and outer cannulas. The hub is further configured to define a first fluid channel connecting the first port with the inner cannula inner lumen and second fluid channel connecting the annular space to the second port. The outer cannula is movable between an extended position where a distal tip of the inner cannula extends well beyond that of the outer cannula and a retracted position in which the outer cannula is closer to the hub. The hub is configured with a flexible channel portion and the outer cannula is affixed to the flexible channel portion of the hub to permit the movement of the outer cannula without sliding engagement of the outer cannula with the hub.

The hub may be of plastic. The flexible channel portion may define a cylindrical channel portion. The flexible channel portion may be deformable with two stable conformations, each corresponding to a respective one of the extended and retracted positions of the outer cannula, whereby the outer cannula snaps from the extended to the retracted position. The hub may include a flange portion extending radially from a point where the outer cannula meets the hub to facilitate moving the outer cannula from the extended position to the retracted position.

According to embodiments, the disclosed subject matter includes a method of using the needle with at least one movable cannula according to the above embodiments, including cannulating a patient with the outer cannula in the extended position, moving the outer cannula to the retracted position after cannulating the patient, and simultaneously infusing and withdrawing blood through the first and second ports, respectively.

According to embodiments, the disclosed subject matter includes a method including withdrawing blood from a patient through a first cannula, infusing blood into a patient through a second cannula, withdrawing blood through a secondary channel affixed to the second cannula such that a withdrawal of the second cannula from the patient is necessarily attended by a disruption of fluid communication through the loss of patency and generating an alarm signal responsively to air being drawn into the secondary channel.

According to embodiments, the disclosed subject matter includes a method of detecting a defective fluid connection including pumping fluid through a fluid circuit having incoming connector under negative pressure and an outgoing connector under positive pressure so the fluid circulates between the incoming and outgoing connectors through the fluid circuit, withdrawing the fluid through the outgoing connector in such a way that a disconnection of the outgoing connector causes inspiration of air into the fluid circuit, and detecting the inspiration of air into the fluid circuit responsively to a disconnection of the outgoing connector and generating a signal responsively thereto.

According to embodiments, the disclosed subject matter includes a vascular access device with a blood circuit having an arterial blood line and a venous blood line. The venous blood line is connected to a first access needle and the arterial blood line being connected to a second access needle. The venous blood line is connected to an access component affixed to the second access needle and configured such that when the second access needle is used to infuse blood into a patient, the access component is positioned to withdraw blood and convey it into the venous line.

The second access needle may be a dual-lumen needle and the access component is a lumen of the dual-lumen needle.

According to embodiments, the disclosed subject matter includes a vascular access device with a blood circuit having an arterial blood line and a venous blood line. The venous blood line is connected to a first access needle and the arterial blood line is connected to a second access needle. The venous blood line is connected to an access component affixed to the second access needle and configured such that when the second access needle is used to infuse blood into a patient. The access component is positioned to withdraw blood and convey it to an air detector.

According to embodiments, the disclosed subject matter includes method of making a dual-lumen needle, comprising: providing a first single lumen needle with a first cannula and hub that supports the first cannula; providing a junction part of having three cylindrical openings, first and second of the openings being coaxial and a third opening having an axis that crosses the common axis of the first two openings; providing a second cannula whose internal diameter is larger than an inner diameter of the first cannula; the first opening having an internal diameter approximately the same as an outer diameter of the second cannula; the second opening being sized and shaped to receive the first hub; and inserting the second cannula in the first opening; inserting the first hub in the second opening including the first cannula with the common axis of the first and second openings; the inserting operations being performed including aligning the first and second cannulas coaxially and forming a seal that defines a channel between the third opening and an annular space between the first and second cannulas; the junction part being configured such that the two inserting operations forms a fluid flow channel joining the third opening for fluid communication with an annular space coaxial with and lying between the first and second cannulas that is isolated from the second port. The inserting of the second cannula may be performed before the inserting the first hub. The inserting of the second cannula may be performed after the inserting the first hub. The forming a seal may include applying epoxy in a position that forms a part of an interior surface of the flow channel. The providing a second cannula may include providing the second cannula supported by a second hub, the combination of the second cannula and the second hub defining a needle with a port configured for attachment to a fluid line, wherein the inserting of the second cannula includes inserting the second hub supporting the second cannula in the first opening. The method may further include solvent bonding the hub to the second opening.

According to embodiments, the disclosed subject matter includes a dual-lumen needle, comprising: an inner cannula having an inner lumen; and an outer cannula having an inner lumen; a hub having first and second ports. The hub may be configured to support the inner and outer cannulas with the outer cannula in coaxial relation to the inner cannula thereby defining an annular channel between the inner and outer cannulas and the hub may be further configured to define a first fluid channel connecting the first port with the inner cannula inner lumen and second fluid channel connecting the annular space to the second port. The inner cannula may be movable between an extended position where a distal tip of the inner cannula extends well beyond that of the outer cannula and a retracted position in which the inner cannula tip is closer to the hub. The hub may be configured with a flexible wall portion remote from the second fluid channel and the inner cannula is affixed to the flexible wall portion of the hub to permit the movement of the inner cannula.

The hub may be of plastic. The flexible wall portion may define an accordion wall shape. The method may further include cannulating a patient with the outer cannula in the extended position, moving the inner cannula to the extended position after cannulating the patient, and simultaneously infusing and withdrawing blood through the first and second ports, respectively.

According to embodiments, the disclosed subject matter includes a dual-lumen needle, comprising: an inner cannula surrounded by an outer cannula both cannulas having sharp tips, there being a gap between the inner and outer cannulas, thereby defining an annular flow channel; the inner cannula extending beyond the outer cannula; a bridging cutter extending between the inner and outer cannulas and positioned such that a cut is made that prevents a separate cut being made in the skin of a patient when the outer cannula enters reaches the skin of a patient as the needle is progressively inserted during cannulation.

The bridging cutter may be aligned radially and parallel with respect to a common access of the inner and outer cannulas. The bridging cutter may be aligned radially and parallel with respect to a common access of the inner and outer cannulas and wherein a cutting edge of the cutter extends diagonally from a cutting edge of the inner cannula to a cutting edge of the outer cannula.

According to embodiments, the disclosed subject matter includes a needle set for a two needle vascular access, comprising: a dual-lumen needle with arterial and venous ports; a single lumen needle with an arterial port; and an arterial line with an arterial connector connected to the single lumen needle arterial port and the dual-lumen needle arterial port; a venous line with a venous connector connected to the venous port.

According to embodiments, the disclosed subject matter includes a needle set for a two needle vascular access, comprising: a first dual-lumen needle with arterial and venous ports; a second dual-lumen needle with arterial and venous ports; an arterial line with an arterial connector connected to the first and second dual-lumen needle arterial ports; and a venous line with an venous connector connected to the first and second dual-lumen needle venous ports.

The cannulas may have blunt tips suitable for buttonhole access. The dual-lumen needles may have an inner cannula extending beyond the outer cannula. The arterial port(s) may be connected to an annular spaced between inner and outer cannulas of the dual-lumen needle(s).

According to embodiments, the disclosed subject matter includes a dual-lumen needle, comprising: an inner cannula surrounded by an outer cannula both cannulas having sharp tips, there being a gap between the inner and outer cannulas, thereby defining an annular flow channel; the inner cannula extending beyond the outer cannula; the outer cannula having a cutting edge at a tip thereof that forms an approximately elliptical contour that lies approximately in a plane forming a diagonal with axis of the outer cannula such that the outer cannula cutting edge has distal-most and proximal-most portions; the inner cannula axis being positioned eccentric of the outer cannula axis such that the inner cannula all is positioned directly adjacent the outer cannula cutting edge distal-most portion.

A resilient spacer may be provided and configured to urge the inner cannula toward the inner wall of the outer cannula.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 7A shows a method and system for using a dual-lumen needle in a blood processing treatment according to embodiments of the disclosed subject matter.

FIG. 7B shows an alternative method and system for using two dual-lumen needles in a blood processing treatment according to embodiments of the disclosed subject matter.

FIG. 7C shows an alternative method and system for using a dual-lumen needle in a blood processing treatment according to embodiments of the disclosed subject matter.

FIG. 7D shows a needle set with a main arterial line and a main arterial line having a secondary arterial branch connected to the main arterial line according to embodiments of the disclosed subject matter.

FIG. 8 shows a dual-lumen needle having another structure according to embodiments of the disclosed subject matter.

FIGS. 9A through 9D show features that may be used with dual-lumen needles according to embodiments of the disclosed subject matter.

DETAILED DESCRIPTION OF THE DRAWINGS

Figure 1A:
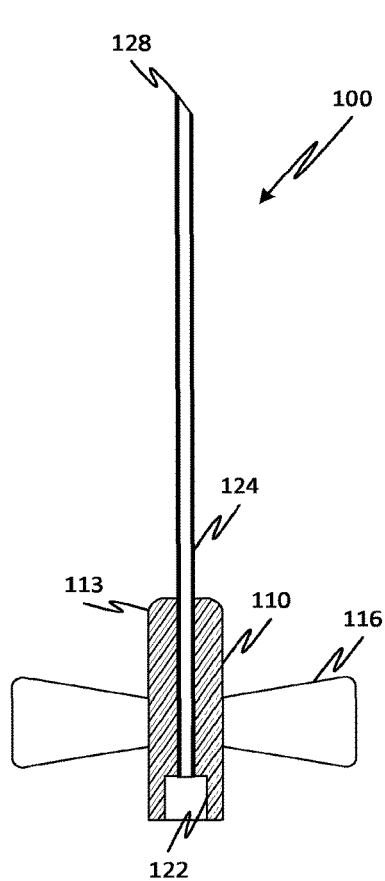
FIGS. 1A and 1B each show a respective single lumen butterfly needle, one selected with a long narrow diameter cannula and the other with a short large diameter cannula according to embodiments of the disclosed subject matter.

FIG. 1A shows a single lumen "butterfly" needle 100 with a long narrow diameter cannula 124 held by a hub 110. The hub 110 has wings 116 on either side to allow the needle 100 to be manipulated more easily, serve as an orienting reference, and allow the needle to be taped down to skin of a patient after cannulation. In embodiments, the needle 100 is what is known as a blunt needle having a fully radius edge at its tip 128 and generally used to access so-called buttonhole type sites. The hub 110 may allow the attachment of a flexible tube (not shown) by means of an internal recess 122 or by inserting the hub 110 into a tube. The cannula 124 may be of metal or other material and may be frictionally engaged with the hub 110, attached by means of fasteners or adhesives or welded to the hub 110 as permitted by the selection of materials.

Figure 1B:
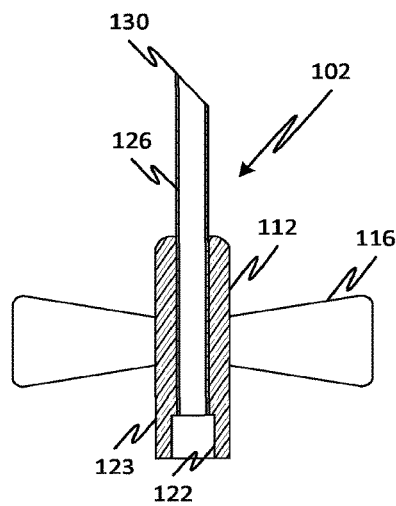
Figure 1C:
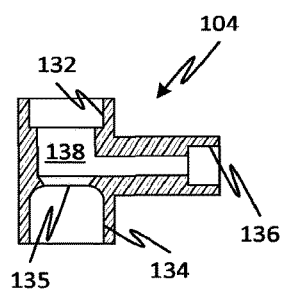
FIG. 1C shows a junction unit allowing the needles of FIGS. 1A and 1B to be combined to form a single dual-lumen needle according to embodiments of the disclosed subject matter.

FIG. 1B shows a single lumen "butterfly" needle 102 with a cannula 126 whose diameter is wider than cannula 124 of FIG. 1A. The cannula 126 is held by a hub 112. The hub 112 has wings 116 on either side. In embodiments, the needle 102 is also a blunt needle having a fully radius edge at its tip 130. The hub 112 may also allow the attachment of a flexible tube by with an internal recess 122 or by inserting the hub into a tube. The cannula 126 may also be of metal or other material and may be frictionally engaged with the hub 112, attached by means of fasteners or adhesives or welded to the hub 112 as permitted by the selection of materials.

Figure 1D:
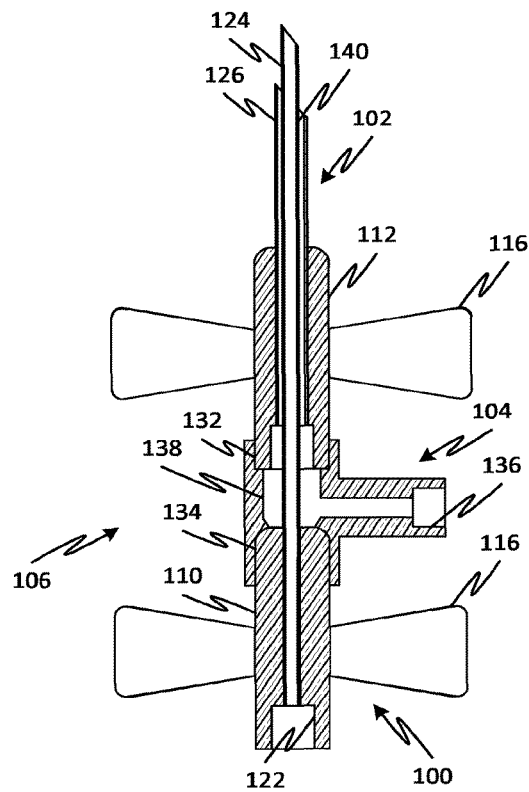
FIG. 1D shows a cross-section of a dual-lumen needle resulting from the combination of components of FIGS. 1A through 1C according to embodiments of the disclosed subject matter.

FIG. 10 shows a junction component 104 into which the needle 100 and 102 hubs 110 and 112 can be inserted to be assembled to form a single dual-lumen needle as shown in FIG. 1D. The junction component 104 has a recess 132 for receiving a heel end 123 of hub 112 of needle 102 and a recess 134 for receiving a top end 113 of hub 110 of needle 100. A branching channel 138 is formed within the junction component 104 that connects the recess 136. To the lumen of cannula 126 as shown in the assembled dual-lumen needle 102 of FIG. 1D.

Figure 6:
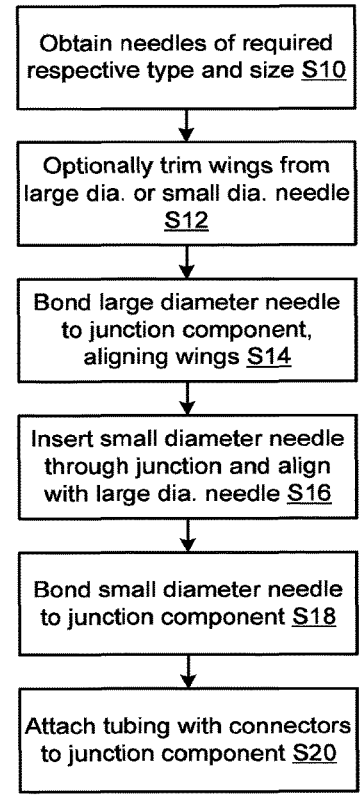
FIG. 6 shows a process for assembling a dual-lumen needle according to embodiments of the disclosed subject matter.

FIG. 1D shows a cross-section of a dual-lumen needle which may be assembled using the process of FIG. 6. Needles of suitable respective sizes 100 and 102 are selected at S10, for example from a vendor catalog. These may be purchased as fully functioning and ready to use or subassemblies from a manufacturer. The needles hubs and cannulas of needles 100 and 102 are pre-assembled, for example, with epoxy.

For example, needle 100 may carry an 18 ga. cannula with an outer diameter of 1.27 mm, a length of 40 mm, and a wall thickness of 0.09 mm. The needle 100 may be a blunt needle. The cannula 124 may or may not have a back eye to promote circulation of blood. The cannula of the needle 100 may also be a sharp cannula instead of a blunt one. Needle 102 may carry a 14 ga. cannula with an outer diameter of 2.11 mm, a length of 24 mm, and a wall thickness of 0.11 mm. The cannula 126 may be a blunt needle. The cannula 126 may or may not have a back eye to promote circulation of blood. The cannula 126 of the needle 102 may also be a sharp cannula instead of a blunt one.

The wings 116 may optionally be trimmed as indicated at S12. For example, the wings 116 of hub 110 or those of hub 112 may be removed or cut off if desired, leaving wings of the other hub intact and accessible for use in cannulation. As indicated at S14, the heel end 123 of hub 112 of needle 102 is inserted in the recess 132 of junction component 104 with, if required, an adhesive material such as epoxy. At S16, the top end 113 of hub 110 of needle 100 is inserted in recess 134 while inserting the cannula 124 through opening 135 and into the cannula 126. At step S18, the hub 110 top end 113 may be attached with, if required, an adhesive material such as epoxy. Solvent welding, thermal welding, interference or friction fits may be used to connect the hubs 110 and 112 to the junction component 104 as well. The opening 135 permits the cannula 124 to be inserted and the opening 125 may be sealed by the bonding of the hub 110 with the junction component 104. Alternatively, a tight fitting opening 135 may form a seal around the cannula 124. Other mechanisms for sealing opening 135 may be used, such as friction welding, a separate gasket, or other devices. In any case, the sealing of opening 135 forms a right-angle channel 138 that connects an annular gap 140 between the cannula 124 and 126 with the port defined by recess 136. In use, this channel may be used for arterial flow of blood (i.e., blood is pumped out of the vascular access through the annular gap 140). The lumen of cannula 124 is directly connected to the port defined by recess 122.

Figure 2:
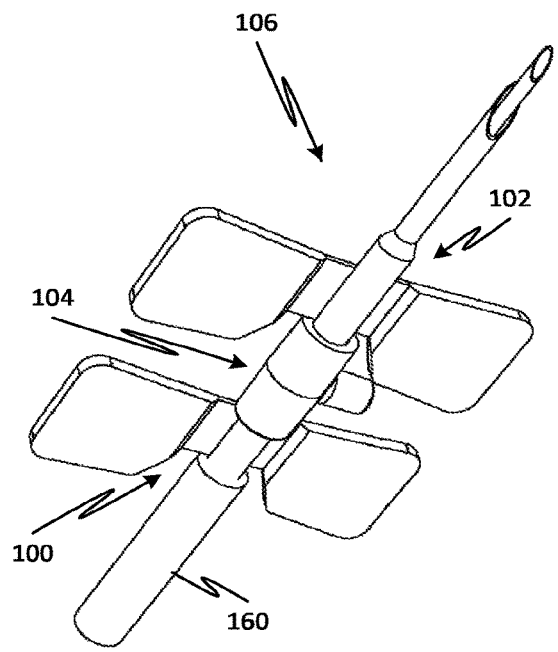
FIG. 2 is a perspective view of the dual-lumen needle similar to that of FIG. 1D.
Figure 5:
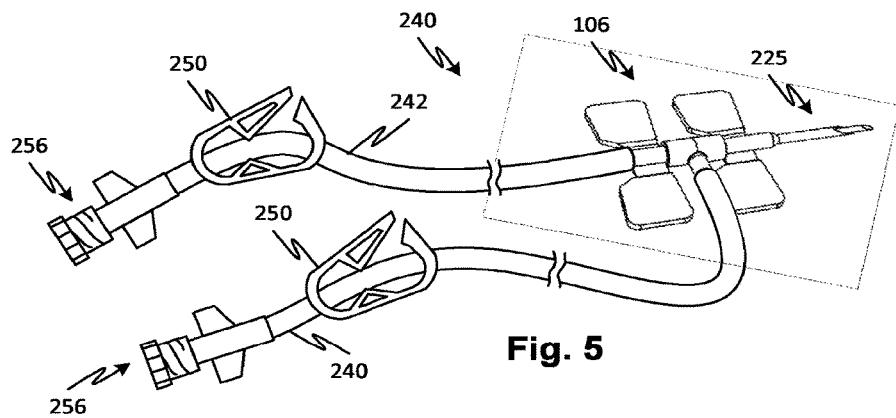
FIG. 5 shows a dual-lumen needle set with venous and arterial lines according to embodiments of the disclosed subject matter.

The completed dual-lumen needle is shown in FIG. 1D at 106 and in FIG. 2 in a perspective view. Tubes 240 and 242 may be attached to the ports 122 and 136, respectively, to form a dual-lumen needle set 240 as illustrated in FIG. 5. The tubes 240 and 242 may carry sealed connectors 256 and clamps 250. A standard cap (not shown but configured to seal the needle 102 and which still may be used since the configuration of the top of the hub 112 remains unchanged and accessible) may be used to seal the dual-lumen needle 225 and the set 240 sterilized as a unit and packaged.

Figure 3C:
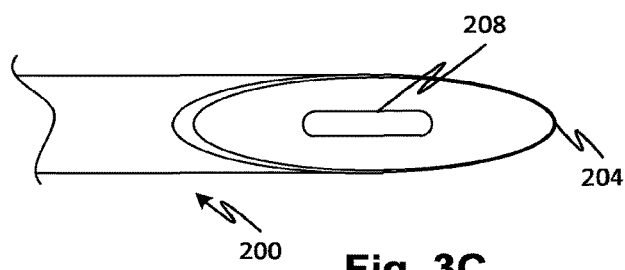
FIG. 3C shows an end view of the buttonhole needle which may be used for an outer cannula of a dual-lumen needle according to embodiments of the disclosed subject matter.
Figure 3A:
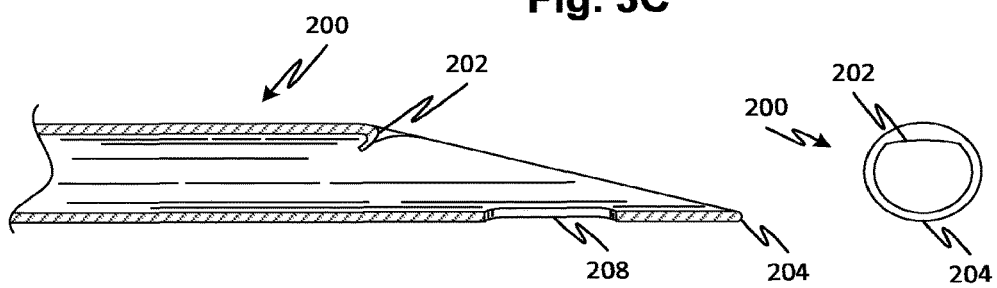
FIG. 3A shows a side section view of a buttonhole needle which may be used for an outer cannula of a dual-lumen needle according to embodiments of the disclosed subject matter.
Figure 3B:
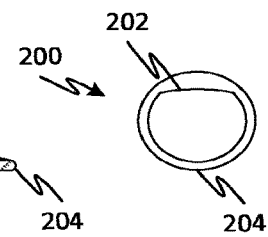
FIG. 3B shows a side view of the end of the buttonhole needle which may be used for an outer cannula of a dual-lumen needle according to embodiments of the disclosed subject matter.

FIG. 3A shows a side section view of a buttonhole needle cannula which may be used for an outer cannula or inner cannula of any of the dual-lumen needle embodiments described herein. Needle 200 has a blunt tip 204 with a full radius as illustrated. A back eye 208 may be provided to promote blood flow. The opening end may have a heel curl 202 or full radii to prevent unwanted cutting of tissue. In any of the disclosed embodiments, the outer cannula (e.g., 126 in FIG. 1D) may have a blunt cannula and inner cannula (124 in FIG. 1D) may be a sharp cannula. In such an embodiment, the inner cannula may cut an opening and the outer cannula may stretch the opening to accommodate it. FIG. 3B shows a side view of the end of the buttonhole needle cannula. FIG. 3C shows an end view of the buttonhole needle cannula.

Figure 4:
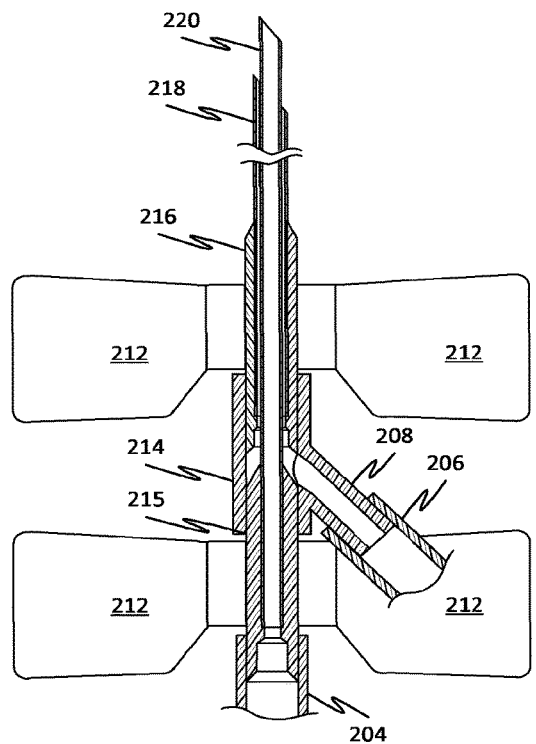
FIG. 4 shows a dual-lumen needle with alternative features according to embodiments of the disclosed subject matter.

FIG. 4 shows a dual-lumen needle with alternative features. As in the foregoing embodiments, an inner cannula 220 is surrounded by an outer cannula 218, with the cannulas being original parts of needles with respective hubs 215 and 216 which are joined by a junction part 214. The junction part 214 has a Y-shape as compared to the T-shape of the dual-lumen needle 106. The lumen of a diagonal branch 208 is in communication with an annular space between the cannulas 218 and 220. Two pairs of wings 212 stem from the respective hubs 215 and 216. Tubes 204 and 206 are fitted to the outside of the hub 215 and the branch 208.

In the foregoing embodiments, two single-lumen needles, each including a hub and a cannula, are connected to form a dual-lumen needle. In embodiments, the dual-lumen needle has concentric cannulas. At least one port may be provided by a junction component. In embodiments, one of the ports is at the base of the needle forming the inner cannula and one extends from the junction component. By utilizing existing subassemblies including at least the hub and cannula of existing needles, a dual-lumen needle may be fabricated from components which benefit from the vast production economies of scale available for the production of single lumen needles that are in very wide use. The end product of a dual-lumen needle takes advantage of the precise manufactured features of the needle subassemblies such as the alignment of the cannulas to their respective hubs and the bonding of the cannula to the hub. The wings of the hubs are accessible in the completed dual-lumen needle for use in the dual-lumen device. In addition, two sets of wings may be provided in the end product which may provide advantages such as easier gripping, stronger tape-down or other benefits.

FIG. 7A shows a method and system for using a dual-lumen needle in a blood processing treatment. In the embodiments illustrated, the dual-lumen needle described above may be used or any other type of dual-lumen needle may be used. For example, dual-lumen needles are described in U.S. Pat. No. 4,134,402 or any other suitable device that ensures that withdrawal of the venous connection (the connection that pumps blood back into the patient's body) is always attended by the disconnection of the arterial line. The needle should be configured such that air will be drawn into the arterial line through the disconnected venous line. Thus, if a recirculation flow could be established by a withdrawn needle, then the configuration of the dual-lumen needle would not be suitable. So for example, in the design of the foregoing embodiments, the inner cannula may be used for returning blood to the patient and the annular space between the cannulas for drawing blood out. Upon withdrawal of the needle a short-circuit flow would be nearly impossible to establish between the annular entry and the tip of the inner cannula and air would surely be drawn in. Alternative configurations are also possible, for example, if the return channel is the annular channel and the withdrawal is through the inner cannula, recirculating flow may be difficult to establish as well.

In the configuration and method shown in FIG. 7A, a needle set 301 shown in FIG. 7D is used. The needle set 301 has a pair of needles, one 320, a conventional single lumen needle 320, for example buttonhole or sharp, is attached to a main arterial line 318. The needle 320 may have, for example, a 15 ga. cannula. Another needle, a dual-lumen needle 322 is attached to a main venous line 316 via one of the needle's 322 lumens (here shown as the lumen of the inner cannula). The other lumen of needle 322 is attached to a secondary arterial branch 314 connected to the common arterial line 303, which is also connected to the main arterial line 318 by a Y junction 319. The needles 320 and 322 may be used in a two-needle access arrangement to be described shortly. The needle set 301 may be packaged in a sterile bag 331 or other packaging along with instructions for using the needle set according to a method as described presently with reference to FIG. 7A.

For coaxial type dual-lumen needles 322, the outer cannula may be 14 ga. and the inner cannula 16, 18, or 20 ga., for example. In any of the embodiments, the tubing 314 for secondary arterial branch 314 is of smaller diameter than the main arterial 318 and venous 314 branches. The secondary arterial branch 314 is used for drawing only enough blood to ensure that the blood does not clot and to ensure that detection of air is established should the dual-lumen needle, which serves primarily the venous return function, be accidentally withdrawn. By providing a smaller diameter tube, any air bubbles will travel along the tube more rapidly to an air detector as described below.

Referring now to FIG. 7A, a patient 308 has a two-needle access employing a needle set 301 as described with reference to FIG. 7D. The main venous line 316 returns blood to the body and the main arterial line 318 draws blood and sends it through the Y junction 319, the common arterial line 303 and into a treatment system 300. Within the treatment system 300 is an air detector 302 and portion of the common arterial line 303 (or a further line connected thereto) which runs through the air detector 302. Any air drawn through the common arterial line 303 is detected by the air detector 302. The air detector (or "bubble detector") is common on the arterial lines of blood treatment systems. The blood treatment system 300 may be one configured for dialysis, hemofiltration, apheresis, ultrafiltration, medication, plasma filtration, plasma substitution, stem cell harvesting, or any kind of blood treatment.

A two needle access is established as indicated at 310. A dual-lumen needle 322 provides mainly venous flow through the inner cannula and via main venous line 316. A small amount of arterial flow is drawn through the annular gap between the inner and outer cannulas in the dual-lumen needle 322 and drawn into common arterial line 303 from arterial branch line 314 via Y junction 319. The lumen of the arterial branch line 314 may be smaller than the other lines to allow air to be drawn quickly through it and to minimize the residence time of blood therein. As a result, of the configuration, if the arterial access is ever lost due to withdrawal (accidental, for example), during pumping of blood, air will be drawn into the common arterial line 303 due to exposure of the annular inlet of the dual-lumen needle 322 to ambient air. The air will be detected by the air detector 302. In this way, but needles of the two-needle access 310 are protected against accidental withdrawal of a needle.

Also, because the annular gap lumen of the dual-lumen needle 322 is primarily used for the detection of withdrawal by inspiration of air, the annular gap may be minimized permitting the venous flow through the dual-lumen needle 322 to be high, as in a single lumen needle. For example, the inner cannula may be a 16 ga. cannula and the outer cannula may be a 14 gage cannula leaving a large inner lumen available for high rate of venous flow. Another benefit is that the potential for short-circuit (recirculating) flow between the inner and outer cannulas is minimized due to the large difference in flow rates.

FIG. 7B shows an alternative method and system for using two dual-lumen needles 322 in a blood processing treatment. Here, the two dual-lumen needles are used for both arterial and venous flow. The machine 300 draws blood through a common arterial line 304 which is connected to the annular lumen of both dual-lumen needles 322 via a respective junction 312 through arterial branch lines 332 and 334. The machine 300 returns blood through a common venous line 305 which is connected to the inner lumen of both dual-lumen needles 322 via a respective junction 312 through venous branch lines 336 and 338. As in the previous embodiment of FIG. 7A, the withdrawal of either needle will cause inspiration of air into the common arterial line 304 and detection by the air detector 302. A corresponding needle set for the FIG. 7B embodiment, similar to needle set 301 (FIG. 7D), may be provided with instructions for use and packaging.

FIG. 7C shows an alternative method and system for using a dual-lumen needle in a blood processing treatment. The system is similar to that of FIG. 7A, except that a separate module 358 is provided that may provide additional functions. The module 358 may include a pump, for example, a peristaltic pump, to regulate the arterial flow through the arterial branch line 314. The module 358 may further have a controller (or connect to one in the treatment machine 300) which provides for variable flow rates of the arterial flow, for example, the flow may be intermittent according to a schedule. In this way, the secure insertion of the dual-lumen needle 322 can be confirmed at regular intervals, for example, every 2 seconds or every 20 seconds or some other schedule. The module 358 may also incorporate an air detector 356 which may allow more immediate detection of a withdrawal of the dual-lumen needle 322. A controller on board the treatment machine 300 may instruct and power the module 356 via a command interface 354 which may be wired or wireless.

A corresponding needle set for the FIG. 7C embodiment, similar to needle set 301 (FIG. 7D), may be provided with instructions for use and packaging. The arterial branch line 314 may include pump segment for engagement with a peristaltic pump rotor. The pump segment may be a portion of tubing that is selected to interoperation with a pump rotor, for example, it may be of a material with different properties from the arterial branch line 314.

FIG. 8 shows a dual-lumen needle 400 having an alternative structure in which the outer cannula 404 is inserted directly in a junction component 402 without an intermediate hub portion. The junction component 402 thus supports the outer cannula 404 directly. The outer cannula 404 may be obtained directly from a supplier or it may be obtained by removing it from a selected needle as obtained according to the method of FIG. 6. This feature of a direct-connected outer cannula may be used in any of the disclosed embodiments. As in some foregoing embodiments, a needle 415 with an inner cannula 408 may be joined via its hub 410 to the junction component 402 such that the lumen between the cannulas 404 and 408 communicates with the port 410 through an internal space 412 defined by the junction component 402.

In any of the embodiments described herein, a sharp tipped inner cannula may be used in conjunction with a blunt tip (buttonhole style) outer cannula. Sharp tips may be difficult to insert or cause damage to the patient's tissue due to the gap between the two cannulas. FIGS. 9A through 9B show features that may be used with sharp tip dual-lumen needles to mitigate these problems in a dual-lumen needle with a sharp outer cannula and a sharp inner cannula. Referring to FIG. 9A, the inner 420 and outer 432 cannulas of a dual-lumen needle 426 are sharp cannulas. A knife 424 may be attached to the inner cannula 420 or the outer cannula 432 or it may be self-supporting in the annular space between. When the dual-lumen needle 426 is inserted, the knife 424 cuts the tissue to prevent the tip of the outer cannula 432 from making a separate opening in the tissue. A similar configuration with a different mutual arrangement of the inner and outer cannulas is shown in FIG. 9B. The knife 428 performs the same function as knife 424.

FIG. 9C shows a dual-lumen needle 425 in end view spacers 434 (typ.) that may be used for separating an inner cannula 421 from an outer cannula 435. The knife 424, 428 is indicated in the end view of FIG. 9C. Spacers may be provided and may be configured in any suitable manner. Spacers may be self-supporting or attached one or both of the inner and outer cannulas. Referring to FIG. 9D, a dual-lumen needle 440 is shown in end view. the inner cannula 44 may be positioned close to the wall of the outer cannula 442, for example by means of a spacer 444. The spacer 444 may be a resilient material configured and arranged to act as a leaf spring, thereby urging the inner cannula toward the wall of the outer cannula. Such an alignment may permit the inner and outer cannulas to work effectively if both have cutting edges at their tips. The inner cannula 44 may alternatively be attached to the inner lumen of the outer cannula 442.

Figure 10A:
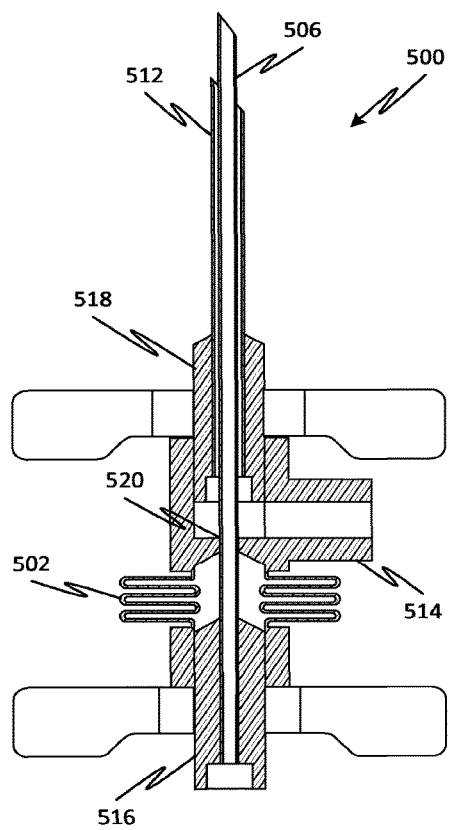
FIGS. 10A and 10B show a dual-lumen needle with an inner cannula that can be retracted and extended according to embodiments of the disclosed subject matter.
Figure 10B:
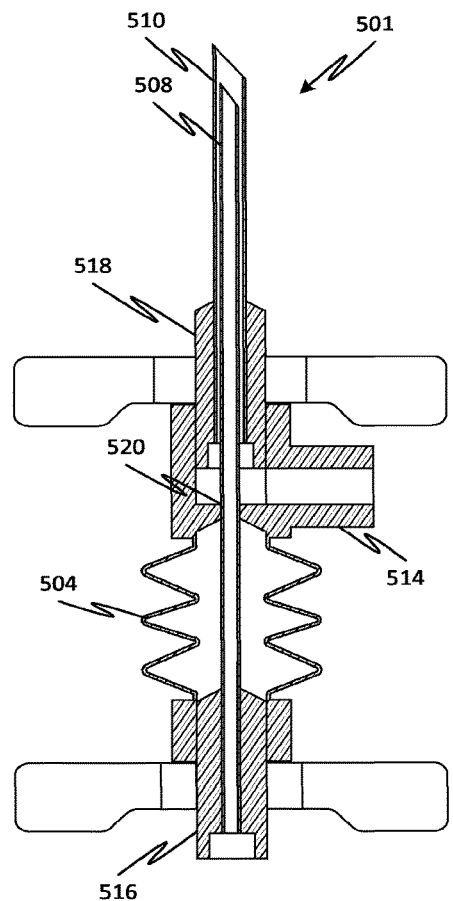

FIGS. 10A and 10B show a dual-lumen needle with an junction component 514 that allows the inner cannula 506 to be retracted and extended relative to the outer cannula 512. The inner and outer cannulas 514 and 512 are attached to respective hubs 516 and 518 and are assembled as needles into the junction component 514 as discussed in the foregoing embodiments. The junction component 514 has a bellows 502 and a compression seal 520 that allow the hub 516 to be retracted for insertion into a patient as shown at 501 in FIG. 10B and then extended as shown at 500 in FIG. 10A. The seal 520 is optional but preferred when the fluid conveyed is blood or otherwise prone to clotting.

Figure 11A:
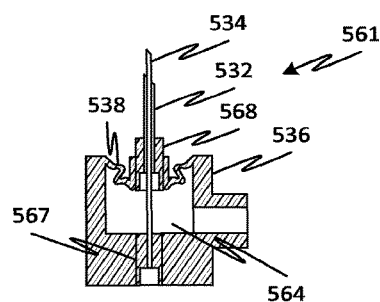
FIGS. 11A and 11B show a dual-lumen needle with an outer cannula that can be retracted and extended according to embodiments of the disclosed subject matter.
Figure 11B:
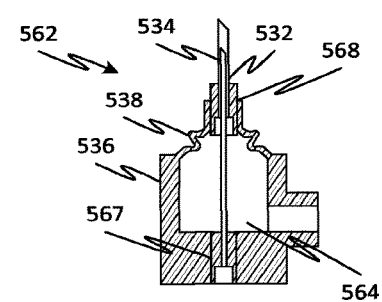

FIGS. 11A and 11B show a dual-lumen needle with an outer cannula that can be retracted and extended. A diaphragm 538 has two stable positions, shown respectively at 561 (outer cannula 532 retracted) and 562 (outer cannula 532 extended). The diaphragm 538 may be provided with concentric accordion folds that are compressed as the outer cannula 532 moves between the extended and retracted positions. The inner and outer cannulas are supported in respective hubs 567 and 568 so that the cannulas are provided as full needle assemblies that are combined with the junction component 536 to form a dual-lumen needle. The cannulas may be sharp and in use the outer cannula 532 may be extended for insertion into tissue and retracted during blood flow. In an alternative embodiment, as in others, the outer cannula or the inner cannula alone may be attached to the junction component and the other of the outer or inner cannula may be attached to the junction component as a needle with a hub. That is, in any of the embodiments, the outer cannula may be directly supported by the junction component rather than using the outer cannula and hub as a complete needle. Also, in any of the embodiments, the inner cannula may be directly supported by the junction component rather than using the inner cannula and hub as a complete needle.

It is, thus, apparent that there is provided, in accordance with the present disclosure fluid conveyance safety devices methods and systems. Many alternatives, modifications, and variations are enabled by the present disclosure. Features of the disclosed embodiments can be combined, rearranged, omitted, etc., within the scope of the disclosed subject matter to produce additional embodiments. Furthermore, certain features may sometimes be used to advantage without a corresponding use of other features. Accordingly, Applicants intend to embrace all such alternatives, modifications, equivalents, and variations that are within the spirit and scope of the present claims.

What is claimed is:

1. A method of providing vascular access, the method comprising:
    withdrawing blood from a patient through a first cannula;
    infusing blood into a patient through a second cannula;
    withdrawing blood through a secondary channel affixed to the second cannula such that a withdrawal of the second cannula from the patient is necessarily attended by a disruption of fluid communication through the loss of patency;
    generating an alarm signal responsively to air being drawn into the secondary channel.

2. The method of claim 1, wherein the second cannula is part of a dual lumen needle.

3. The method of claim 1, wherein said generating an alarm signal includes passing blood resulting from said withdrawing blood through a secondary channel through an air detector.

4. The method of claim 1, further comprising infusing blood through a second channel affixed to the first cannula.

5. The method of claim 1, wherein the secondary channel and the second cannula are coaxial cannulae.

6. The method of claim 1, wherein the first cannula is a dual lumen cannula.

7. The method of claim 1, wherein blood withdrawn through the first cannula and the secondary channel are combined into a single flow and conveyed to an air detector.

8. The method of claim 1, wherein blood withdrawn through the first cannula and the secondary channel are pumped through a junction to form a single flow which is conveyed to an air detector.

9. The method of claim 8, further comprising conveying the blood from the air detector to a blood treatment device.

10. A vascular access device, comprising:
    a blood circuit having an arterial blood line and a venous blood line;
    the venous blood line being connected to a first access needle and the arterial blood line being connected to a second access needle;
    the venous blood line being connected to an access component affixed to the second access needle and configured such that when the second access needle is used to infuse blood into a patient, the access component is positioned to withdraw blood and convey it into the venous line.

11. The device of claim 10, wherein second access needle a dual-lumen needle and the access component is a lumen of the dual-lumen needle.

12. The device of claim 10, wherein the second access needle includes a dual lumen needle set and the access component is a lumen thereof.

13. The device of claim 10, wherein the blood circuit is shaped to be engaged the venous blood line to a predefined blood pump in a predefined orientation that causes blood to be drawn from the first access needle when the pump is operated.

14. The device of claim 10, wherein the venous blood line is connected to the access component through a tube junction.

15. A vascular access device, comprising:
    a blood circuit having an arterial blood line and a venous blood line; the venous blood line being connected to a first access needle and the arterial blood line being connected to a second access needle;
    the venous blood line being connected to an access component affixed to the second access needle and configured such that when the second access needle is used to infuse blood into a patient, the access component is positioned to withdraw blood and convey it to an air detector.

16. A needle set for a two needle vascular access, comprising:
    a dual-lumen needle with arterial and venous ports;
    a single lumen needle with an arterial port; and
    an arterial line with an arterial connector connected to the single lumen needle arterial port and the dual-lumen needle arterial port;
    a venous line with a venous connector connected to the venous port.

* * * * *